United States Patent [19]

Wagner et al.

[11] Patent Number: 5,350,862

[45] Date of Patent: Sep. 27, 1994

[54] PROCESS FOR THE PREPARATION OF ETHYLENE GLYCOL CARBONATE

[75] Inventors: Paul Wagner, Duesseldorf; Hans-Josef Buysch, Krefeld; Alexander Klausener, Stolberg; Franz-Josef Mais, Duesseldorf; Christine Mendoza-Frohn, Erkrath, all of Fed. Rep. of Germany

[73] Assignee: Bayer Aktiengesellschaft, Leverkusen, Fed. Rep. of Germany

[21] Appl. No.: 984,789

[22] Filed: Dec. 3, 1992

[30] Foreign Application Priority Data

Dec. 13, 1991 [DE] Fed. Rep. of Germany ....... 4141189

[51] Int. Cl.$^5$ .................. C07D 317/36; C07D 317/38
[52] U.S. Cl. ........................................ 549/230
[58] Field of Search .......................... 549/230

[56] References Cited

U.S. PATENT DOCUMENTS

| | | | |
|---|---|---|---|
| 4,314,945 | 2/1982 | McMullen et al. | 549/230 |
| 4,325,874 | 4/1982 | Jacobson | 549/230 |
| 4,786,741 | 11/1988 | Sachs | 549/230 |
| 5,091,543 | 2/1992 | Grey | 549/230 |
| 5,138,073 | 8/1992 | Harvey | 549/230 |

OTHER PUBLICATIONS

Dr. H. Springmann, *Fette Seifen Anstrichmittel*, 1971, pp. 396–398.

Primary Examiner—Emily Bernhardt
Attorney, Agent, or Firm—Sprung Horn Kramer & Woods

[57] ABSTRACT

A process is described for the catalytic preparation of ethylene glycol carbonate by reaction of ethylene oxide and $CO_2$ in ethylene glycol carbonate as the reaction medium at elevated temperature and at elevated pressure with work-up by distillation to separate the resulting ethylene glycol carbonate from the catalyst. The process is carried out continuously under adiabatic temperature conditions. Per unit of time, ethylene glycol carbonate as reaction medium runs into the reactor in a amount 10 to 120 times that of ethylene glycol carbonate formed per unit of time. A $CO_2$ excess over the other reaction partner ethylene oxide is maintained at all sites of the reactor. 80 to 98% by weight of the reaction mixture flowing out is returned to the inlet of the reactor, while the remainder is worked up by distillation to give ethylene glycol carbonate. The sensible heat produced in the reaction product as a result of the adiabatic temperature conditions, is used for the work-up.

19 Claims, 1 Drawing Sheet

PROCESS FOR THE PREPARATION OF ETHYLENE GLYCOL CARBONATE

BACKGROUND OF THE INVENTION

The present invention relates to a process for the continuous catalytic preparation of ethylene glycol carbonate (EGC) from ethylene oxide (EOX) and carbon dioxide ($CO_2$), which is characterised by a procedure which is adiabatic and particularly mild, energy-saving and material-saving.

Many proposals have been made regarding the preparation of EGC. These relate in the main to the use of certain catalysts. An extensive account of this is to be found in Fette, Seifen, Anstrichmittel 73, (1971), 396 ff. Adiabatic temperature conditions are described in this account as not being technically feasible (loc. cit. 398). In the process described there, $CO_2$ and EOX are reacted together at 80 bar and 190 to above 200° C. in a reactor filled with ethylene glycol carbonate, and the heat of reaction is conducted away with the aid of a heat carrier circulating in counter-current which itself is cooled using water. Under these reaction conditions, peak temperatures of up to 220° C. in the reactor are obtained, which can be harmful to the product, which is expressly referred to in the cited publication (p. 397), and which would be difficult to overcome in particular in industrial large-scale plants. The overall energy of reaction is conducted away unutilised in this case. Adiabatic temperature conditions, in contrast to this, are characterised in that all of the heat of reaction evolved is taken up by the reaction mixture itself; in the case of exothermic reactions this leads to increase in the temperature of the reaction mixture.

It was desired to develop a process which on the one hand avoids harmful temperature peaks and on the other hand utilises the energy of reaction as far as possible, either in the novel process itself, for example to obtain EGC by distillation, or to generate heating steam for other processes.

SUMMARY OF THE INVENTION

A process has been found for the catalytic preparation of ethylene glycol carbonate by reaction of ethylene oxide and carbon dioxide in ethylene glycol carbonate as the reaction medium at elevated temperature and elevated pressure with work-up by distillation to separate the resulting ethylene glycol carbonate from the catalyst, which is characterised in that a) the process is carried out continuously and adiabatically at a pressure of 2 to 200 bar, preferably 5 to 80 bar, particularly preferably 8 to 60 bar, and within a temperature range of 110° to 200° C., preferably 110° to 190° C., particularly preferably 110° to 180° C., with an adiabatic temperature increase of 5° to 80° C., the inlet temperature being selected in such a manner that the adiabatic temperature increase remains within the temperature range mentioned, b) the ethylene glycol carbonate running into the reactor per unit of time as reaction medium is 10 to 120 times the ethylene glycol carbonate formed in this unit of time, c) 1.01 to 1.3 mol, preferably 1.01 to 1.25 mol, particularly preferably 1.01 to 1.2 mol, of carbon dioxide are used per mole of ethylene oxide and a carbon dioxide excess is maintained at all sites of the reactor, d) 80 to 98% by weight, preferably 85 to 97% by weight, particularly preferably 88 to 97% by weight, of the total reaction mixture is returned to the inlet of the reactor and the remainder is worked up by distillation to give ethylene glycol carbonate, and e) the sensible heat produced in the reaction mixture as a result of the adiabatic process conditions is utilised for the work-up of the reaction mixture.

DETAILED DESCRIPTION OF THE INVENTION

The starting materials EOX and $CO_2$ are generally used in a purity of at least 99%. However, it is equally possible to use EOX and $CO_2$ in a lower purity if the remainder up to 100% is composed of inert substances, such as, for example, hydrocarbons, carbon monoxide or nitrogen. This applies particularly to $CO_2$, which can originate from various sources, for example from natural sources or from plants for producing water gas, carbon monoxide or reformers and is correspondingly of lower purity. However, such inert gases are expediently present in an amount not greater than 10% by volume, preferably not greater than 5% by volume, particularly preferably not greater than 3% by volume.

The catalysts used can be virtually all those previously proposed, such as alkali metal bromides and alkaline earth metal bromides and alkal metal iodides and alkaline earth metal iodides, guanidines and their hydrobromides or hydroiodides, tetraalkylanunonium bromides and tetraalkylammonium iodides, phosphonium bromides and phosphonium iodides, pyridinium halides, sulphonium, stibonium and arsonium halides, zinc halides and lead halides, alkyltin compounds or mixtures of alkali metal halides with halides of divalent metal ions (FR 1 538 576; BE 872 960; EP 297 647; US 3 535 342; US 2 773 070; US 2 994 705; DE 15 43 555; US 3 535 41; BE 798 171; BE 872 959; Deutsche Offenlegungsschrift 32 44 456; GB 2 098 985; EP 133 763; EP 180 387; J. Org. Chem. 45 (1980), 3735; Chem. Lett. 1979, 573; Deutsche Offenlegungsschrift 41 05 554). Catalysts preferably used are: alkali metal bromides and alkali metal iodides, tetraalkylammonium bromides and tetraalkylammonium iodides, phosphonium halides, guanidinium halides and mixtures of alkali metal halides with halides of divalent metals.

The process is carried out in the temperature range of 110° to 200° C., preferably 110 to 190° C., particularly preferably 110 to 180° C. The pressure for the process according to the invention is 2 to 200 bar, preferably 5 to 80 bar, particularly preferably 8 to 60 bar; at temperatures in the upper part of the range given, pressures in the upper part of the range given are also used and vice versa.

The process according to the invention is carried out using adiabatic temperature conditions, so that the adiabatic temperature increase is 5° to 80° C. The inlet temperature is chosen in this case in such a manner that even with complete utilisation of the chosen adiabatic temperature increase, the upper limit of the temperature range given for the overall process is not exceeded.

According to the invention, a $CO_2$ excess over the other reaction partner EOX is maintained at all sites of the reactor. For this purpose, 1.01 to 1.3 mol, preferably 1.01 to 1.25 mol, particularly preferably 1.01 to 1.2 mol, of $CO_2$ are used per mole of EOX.

EGC as reaction medium is always present in a large excess over the newly formed EGC. Thus, per unit of time, 10 to 120 times the amount of EGC formed in this unit of time runs into the reactor as circulating EGC, which also contains the catalyst. This large excess is further maintained in that 80 to 98% by weight, preferably 85 to 97% by weight, particularly preferably 88 to 97% by weight, of the total reaction mixture is returned to the inlet of the reactor and only the remainder to 100% is withdrawn and worked up by distillation to give pure EGC.

A further characteristic of the process according to the invention is that the sensible heat produced in the reaction mixture as a result of the adiabatic temperature conditions is utilised. The most important possible utilisation is for work-up of the reaction mixture to give pure EGC. However, the amount of sensible heat produced in the reaction product is generally so great that heating steam can be additionally generated and be supplied to other (endothermic) processes. To recover the sensible heat here, the reaction mixture is cooled in a preferred manner by 5° to 60° C., preferably by 10° to 50° C., particularly preferably by 10 to 40° C.

Turbulent flow is maintained in the reactor to avoid undesirable temperature peaks.

BRIEF DESCRIPTION OF THE DRAWING

Further details of the process according to the invention are described below, in which context reference is also made to the accompanying FIG. 1, which shows a possible illustrative embodiment of the process according to the invention. Procedural variants other than that in FIG. 1 are, of course, also possible.

The reactor (I) is a well-insulated apparatus, for example a well-insulated tubular reactor; it contains internals which ensure a continuous good distribution of the gases EOX and $CO_2$ metered in and produce turbulence at all sites. Such internals, which are known to those skilled in the art, are for example perforated plates, perforated trays and baffle trays, tube distributors (elongated and ring distributors), two-fluid nozzles, jet nozzles, nozzle trays, nozzles according to German Offenegungsschrift 37 36 988 (equivalent to U.S. Pat. No. 4,851,570) and German Offenlegungsschrift 37 44 001 (equivalent to U.S. Pat. No. 5,117,048), industrially conventional aeration trays, sintered metal frits, closed gas distributor trays having permeation orifices for the EGC, rotating aeration apparatuses, impingement aerator elements (Perrys Chemical Engineer's Handbook 1984 p. 18.57–18.70), mixer elements, sheet metal internals to increase the turbulence, segment baffles and annular baffles. These internals can also be used in combination with each other. In general, such internals should produce, in addition to thorough mixing of the flow (macromixing) and the fine gas distribution, the highest possible fraction of high-frequency turbulence elements in the dissipation range. Preferred internals are perforated trays, pipe distributors, two-fluid nozzles, jet nozzles, nozzles according to German Offenlegungsschrift 37 36 988 (equivalent to U.S. Pat. No. 4,851,570) and German Offenlegungeschrift 37 44 001, (equivalent to U.S. Pat. No. 5,117,048), closed gas distributors, impingement aerator elements and mixer elements.

Figure 1:
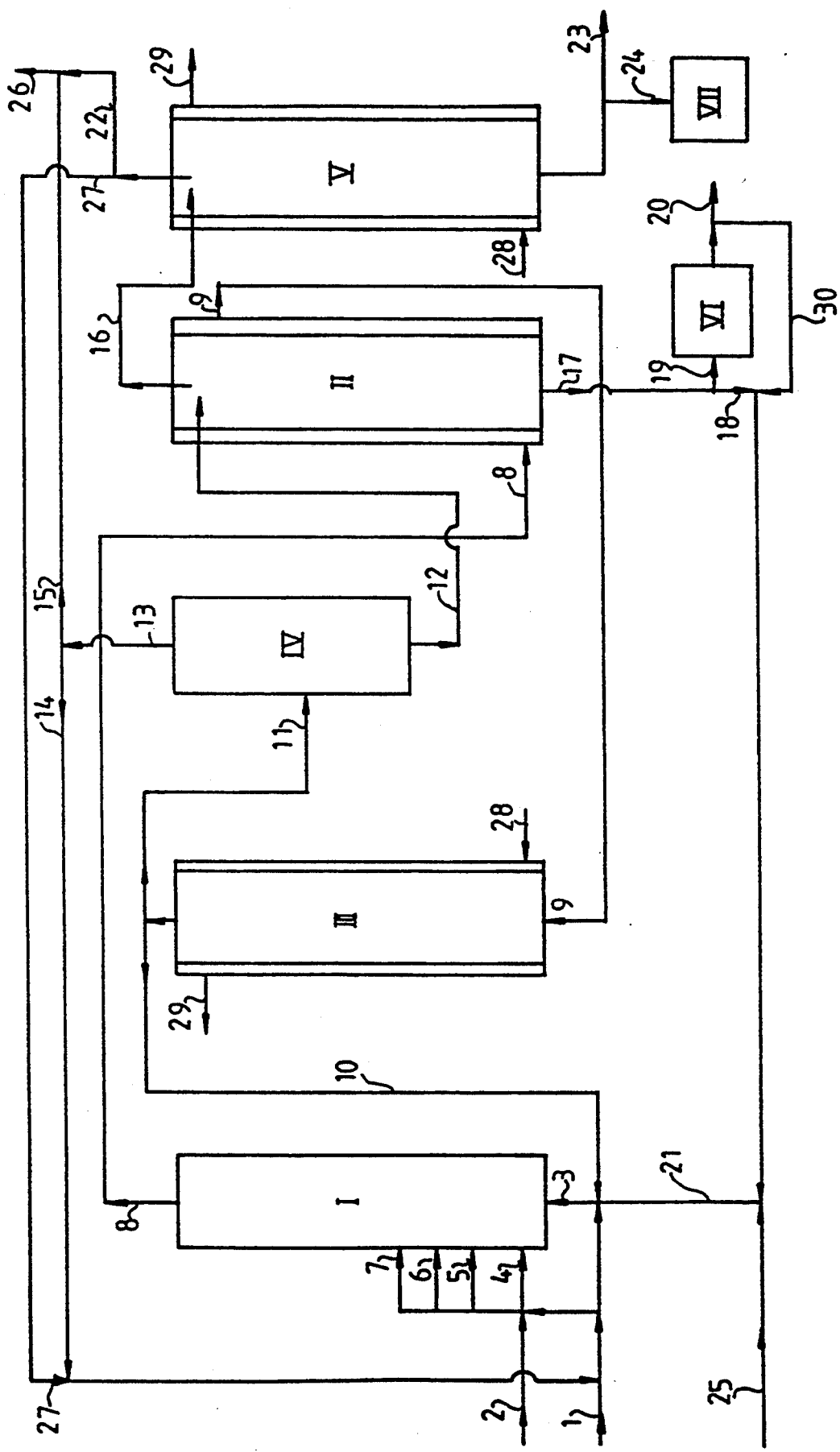

$CO_2$ in the process according to the invention, according to the procedural variant of FIG. 1, is supplied at (1) and EOX at (2).

Since it is important for the high selectivity of the reaction according to the invention, that EOX meets $CO_2$ everywhere in the reactor and itself occurs nowhere in excess or even simply at high concentrations, $CO_2$ is fed into the reactor prior to the EOX and in the direction of flow. At least some of the $CO_2$ is fed prior to the EOX is fed in this way, while the remainder of the $CO_2$ is fed in one or more part-quantities to further positions of the reactor in such a manner that $CO_2$ is always present in excess over the EOX. In a preferred variant, according to FIG. 1, all or some of the $CO_2$ is mixed, even before entry into the reactor, with the EGC (3), which already contains the catalyst, flowing into the reactor. In a preferred manner, this preadmixture of $CO_2$ relates to the excess of $CO_2$ in the sense of the abovedescribed $CO_2$ excess of 1 to 30 mol % over the amount of the EOX. EOX is only added at a later entry site (4), preferably in a mixture with $CO_2$; such a mixture is particularly preferably composed of equimolar quantities of EOX and $CO_2$. In a further preferred manner, an EOX/$CO_2$ mixture is fed into the reactor at at least two feed sites. At least a second such feed site is (5), further feed sites can be (6) and (7) and also others. These fed gases are then distributed uniformly in the reaction medium with the aid of the abovementioned internals (distributor means). The relatively large number of feed sites (4), (5), (6), (7) and others avoids local excess concentrations and local temperature peaks in the reactor.

After the main reaction in the reactor (I) has subsided, the reaction mixture (8) flows into the heating jacket of the flash evaporator (II) to utilise the sensible heat and flows from there as a cooled reaction mixture (9) for further utilisation through a heat exchanger (III) in which heating steam (29) is recovered from water (28). However, the outflow (8) of the reactor can first be passed through the heat exchanger (III) and then through the heating jacket of the flash evaporator (II). Alternatively, a reactor, to be heated, of a completely different process, the reaction of which proceeds endothermically, can replace the heat exchanger (III) producing the heating steam. However, the outflow (8) can alternatively be divided, prior to entry into the flash evaporator (II), into part-streams, corresponding to (10) and (11).

The passages through (II) and (III) simultaneously denote for the reactor outflow (8) and the already somewhat cooled reaction mixture (9) a period serving for the post-reaction time.

The still further cooled reaction mixture leaving the heat exchanger (III) in the example of FIG. 1, the sensible heat of which mixture has decreased overall by the abovementioned amount of 5° to 80° C., is now divided into the part-streams (10) and (11) The part-stream (10) includes, in the manner already described above, 80 to 98% by weight of the total outflow of the reactor (I); the part-stream (11) represents the remainder to 100%. Of course, it is possible in principle to carry out the division of (9) into the part-streams (10) and (11) at another site of the process course.

While the part-stream (10) is returned to the reactor inlet, the part-stream (11) is fed to the work-up. For this purpose, (11) is first passed into a flash vessel (IV), in which a separation takes place into liquid (12) and a gas phase (13). The gas phase (13) contains excess $CO_2$ with or without incompletely reacted EOX and inert gases possibly introduced with the $CO_2$ and the EOX. Depending on the fraction of inert gases, the gas phase (13) is divided into the two part-streams (14) and (15). (14) is returned to the reactor, while (15) is fed to the exhaust gas disposal (26). Of course, in the case of relatively high inert gas contents a higher fraction of (13) is ejected in the form of the part-stream (15) and vice versa; simple analytical determinations and calculations and preliminary trials give the optimum for division of the gas phase (13) without any difficulty for those skilled in the art.

The liquid (12) separated off in (IV) is then passed into the interior of the flash evaporator (II). The flash evaporator (II) is preferably a thin film evaporator, a falling film evaporator, a spiral tube evaporator or a rotary or climbing film evaporator. In (II), at a vacuum of 2 to 100 mbar, preferably 8 to 90 mbar, particularly preferably 10 to 80 mbar, a separation by distillation is carried out into vapourised EGC (16) and a liquid bottom product (17). The energy for this separation by distillation originates on the one hand from the reactor outflow (8), which is passed through the jacket or other heating device of the flash evaporator (II), and on the other hand from the remaining internal sensible heat of the liquid phase (12).

The bottom product (17) of (II) is divided into the partstreams (18) and (19). By far the greatest amount, for example 60 to 98%, preferably 75 to 97%, particularly preferably 90 to 96%, of the total amount of (17) returns as part-stream (18) to the reactor inlet.

This also contains the catalyst. This furthermore closes the circulation of the EGC acting as reaction medium circulated in the reactor system.

The remaining part-stream (19) flows to a regeneration possibility (VI) for the catalyst. The type of regeneration of the catalyst is specifically tailored to the particular catalyst used and, as far as a catalyst regeneration is at all possible, is known to those skilled in the art from the abovementioned literature. A fraction of the catalyst (20) which has become virtually inactive can be discharged from the regeneration (VI). The regenerated catalyst is returned to the reactor inlet in a mixture with EGC (30) exactly as is the part-stream (18). The regeneration can be carried out in such a manner for example that catalysts of the type of mixtures of alkali metal halides with halides of divalent metals, such as NaBr/ZnBr$_2$, are treated with halogen compounds, such as HBr.

Replenishment of used and discharged catalyst by fresh catalyst (25) passes via (21) into the reactor.

The distilled-off EGC (16) leaving the interior of (II) is condensed in a further heat exchanger (V) with vapour recovery and is cooled to a temperature which is required for further reactions, for example for reesterification with methanol to give dimethyl carbonate. Such a condensed EGC is withdrawn at (23). Of course, the EGC can alternatively be further cooled and fed as (24) to a storage tank (VII).

Any gaseous fractions of (12), which were brought with evaporated (16) to (V), occur in (V) on the condensation of EGC as a gaseous stream, to be withdrawn via the head, which is divided into the two part-streams (22) and (27). (22) is fed to the exhaust gas disposal (26), while (27) is returned to the reactor inlet. The division into the part-streams (22) and (27) takes place under the imposition of similar criteria such as have already been described above for the part-streams (14) and (15).

(28) the water, fed to the heat exchangers (III) and (V), can be removed from these apparatuses as heating steam (29) produced by utilisation of the heat of evaporation or sensible heat.

EXAMPLE

In the reactor I according to FIG. 1 operated at 15 bar, a total of 0,527 kg of CO$_2$ is metered in per hour via (1) and a total of 0.504 kg of EOX is metered in per hour via (2), more precisely in such a manner that 0,126 kg of CO$_2$ and of EOX flow as a mixture through each of the lines (4) to (7) and 0.023 kg of CO$_2$ is admixed (3) to about 30.2 kg of the reaction mixture having a temperature of 140° C. returning via (10) prior to entry into the reactor I. From the decompression stage IV, a further 0-03 kg of gas flows via (13) and (14) into the reactor I.

After the course of the reaction, 31.8 kg of the reaction mixture having a temperature of about 160° C. leave the reactor and flow as stream (8) into the jacket of the flash evaporator II, which they leave with a temperature of about 151° C. after heating the distillation occurring therein, and flow as stream (9) into heat exchanger III, which they leave at a temperature of about 140° C. after production of steam, and are then divided into stream (10) of about 30.2 kg and (11) of about 1.6 kg. (10) returns, as described, into the reactor, while (11) is decompressed to 1 bar in IV, the gaseous phase (13) of 0.03 kg being passed to I and the liquid phase (12) of 1.57 kg being passed to the flash evaporator II, where it is separated at about 40 mbar into approximately 1.03 kg of vapour phase EGC (16) and about 0.54 kg of bottom product (17). The 0.03 kg of remaining gas escaping in this is withdrawn via (22) and (26) into the exhaust gas disposal. EGC (16) condenses in the heat exchanger V with production of steam and cools to a temperature in the range 70°–110° C., as is desired (23) for a reesterification, for example to give dimethyl carbonate.

After division of the bottom product (17) corresponding to about 9:1, the greater amount of approximately 0.49 kg flows as stream (18) and (21) to I and the smaller amount of about 0.05 kg (19) into the regeneration VI, which, following treatment with a very small amount of a halogen compound, it leaves again as (30) and is returned as (21) into the reactor.

What is claimed is:

1. A process for the catalytic preparation of ethylene glycol carbonate by reaction of ethylene oxide and carbon dioxide in ethylene glycol carbonate as the reaction medium at elevated temperature and elevated pressure with work-up to separate the resulting ethylene glycol carbonate from the catalyst, wherein
   a) the process is carried out continuously and adiabatically at a pressure of 2 to 200 bar and within a temperature range of 110° to 200° C., with an adiabatic temperature increase of 5 to 80° C, the inlet temperature being selected in such a manner that the adiabatic temperature increase remains within the temperature range mentioned,
   b) the ethylene glycol carbonate running into the reactor per unit of time as reaction medium is 10 to 120 times the ethylene glycol carbonate formed in this unit of time,
   c) 1.01 to 1.3 mol of carbon dioxide are used per mole of ethylene oxide and a carbon dioxide excess is maintained at all sites of the reactor.
   d) 80 to 98% by weight of the total reaction mixture is returned to the inlet of the reactor and the remainder is worked up to give ethylene glycol carbonate.

2. The process of claim 1, which is carried out at a pressure of 5–80 bar.

3. The process of claim 2, which is carried out at a pressure of 8–60 bar.

4. The process of claim 1, which is carried out within a temperature range of 110° to 190° C.

5. The process of claim 4, which is carried out within a temperature range of 110°–180° C.

6. The process of claim 1, wherein a turbulent flow is maintained in the reactor.

7. The process of claim 6, wherein the reactor contains perforated trays, pipe distributors, two-liquid nozzles, jet nozzles, closed gas distributors, impingement aerator elements, mixer elements or a combination of a plurality thereof.

8. The process of claim 1, wherein, to produce the carbon dioxide excess, at least some of the carbon dioxide is fed into the ethylene glycol carbonate, acting as reaction medium, prior to the injection of the ethylene oxide.

9. The process of claim 8, wherein the carbon dioxide fed prior to the injection of the ethylene oxide is added to the ethylene glycol carbonate prior to entry into the reactor.

10. The process of claim 8, wherein ethylene oxide is fed into the reactor alone or as a mixture with or without remaining carbon dioxide at at least two sequential sites in such a manner that a carbon dioxide excess always exists.

11. The process of claim 10, wherein the intended excess of carbon dioxide is added to the ethylene glycol carbonate prior to its entry into the reactor and the remaining carbon dioxide is fed as an equimolar ethylene oxide/carbon dioxide mixture into the reactor.

12. The process of claim 1 wherein said workup is by distillation and the sensible heat produced in the reaction mixture as a result of the adiabatic-temperature increase is utilized in said distillation.

13. The process of claim 12, wherein the sensible heat achieved of the reaction mixture, is additionally used to generate heating steam.

14. The process of claim 13, wherein in the recovery of the sensible heat, a cooling of the reaction mixture by 5° to 80° C. occurs.

15. The process of claim 14, wherein a cooling of the reaction mixture by 10° to 50° C. occurs.

16. The process of claim 15, wherein a cooling of the reaction mixture by 10° to 40° C. occurs.

17. The process of claim 13, wherein the work-up by distillation to give ethylene glycol carbonate with utilisation or the recovered sensible heat is carried out at 2 to 100 mbar.

18. The process of claim 17, wherein the work-up is carried out at 8 to 90 mbar.

19. The process of claim 18, wherein the work-up is carried out at 10 to 80 mbar.

* * * * *